United States Patent
Levene et al.

(10) Patent No.: US 7,418,082 B2
(45) Date of Patent: Aug. 26, 2008

(54) ANTI-SCATTERING X-RAY COLLIMATOR FOR CT SCANNERS

(75) Inventors: Simha Levene, D.N. Hanegev (IL); Avner Elgali, Tzur Yigal (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 162 days.

(21) Appl. No.: 10/558,765

(22) PCT Filed: Jun. 1, 2003

(86) PCT No.: PCT/IL03/00453

§ 371 (c)(1),
(2), (4) Date: Nov. 30, 2005

(87) PCT Pub. No.: WO2004/107355

PCT Pub. Date: Dec. 9, 2004

(65) Prior Publication Data

US 2007/0025518 A1    Feb. 1, 2007

(51) Int. Cl.
*G21K 1/02* (2006.01)
(52) U.S. Cl. .................................. 378/154; 378/147
(58) Field of Classification Search .............. 378/147, 378/149, 154, 155
See application file for complete search history.

(56) References Cited

U.S. PATENT DOCUMENTS

| | | | |
|---|---|---|---|
| 3,921,000 A * | 11/1975 | Muehllehner | 378/149 |
| 3,943,366 A * | 3/1976 | Platz et al. | 378/149 |
| 4,054,800 A | 10/1977 | Leask | 250/505 |
| 4,057,726 A * | 11/1977 | Jaszczak | 250/363.04 |
| 4,450,706 A | 5/1984 | Engelmohr | 72/385 |
| 6,137,857 A | 10/2000 | Hoffman et al. | 378/19 |
| 6,363,136 B1 | 3/2002 | Flisikowski et al. | 378/154 |
| 6,707,884 B1 * | 3/2004 | Ogawa | 378/154 |
| 7,099,428 B2 * | 8/2006 | Clinthorne et al. | 378/17 |

FOREIGN PATENT DOCUMENTS

| | | |
|---|---|---|
| JP | 2001-212128 | 8/2001 |
| JP | 2002-82175 | 3/2002 |
| WO | WO 2004/023123 | 3/2004 |

OTHER PUBLICATIONS

Schnopper, H.W., et al.; Joint European X-Ray Monitor (JEM-X):X-ray monitor for ESA's Integral Mission; 1996; SPIE; 2806:297-307.

* cited by examiner

*Primary Examiner*—Hoon Song

(57) ABSTRACT

An X-ray collimator for collimating X-rays from an X-ray source that illuminate an array of columns and rows of X-ray detectors, the collimator having a first side that faces the X-ray source and a second side opposite the first side that faces the detector array, the collimator comprising: a plurality of strips formed from an X-ray absorbing material, wherein each strip is corrugated so that it has rectangular and/or square corrugations; and means for maintaining the plurality of strips one next to the other with the corrugations of one strip aligned with corrugations of an adjacent strip to form an array of rows and columns of square/and or rectangular wells corresponding to the X-ray detectors in the array.

20 Claims, 11 Drawing Sheets

ANTI-SCATTERING X-RAY COLLIMATOR FOR CT SCANNERS

FIELD OF THE INVENTION

The present invention relates to computerized tomography (CT) X-ray imaging and in particular to shielding for X-ray detectors in a CT imaging system that protects the detectors from scattered X-rays.

BACKGROUND OF THE INVENTION

A multislice CT scanner for imaging a region of interest (ROI) of a patient comprises an X-ray source that provides a cone-shaped X-ray beam radiated from a focal spot of the X-ray source and a detector array comprising rows and columns of X-ray detectors. The detector array is positioned facing the X-ray source and receives X-rays from the X-ray source that pass through the patient's body. The X-ray source and detector array are mounted on a rotor of a gantry and the patient is supported on an appropriate support couch. The couch is moveable axially, along an axis referred to as a "z-axis", relative to the gantry and the rotor is rotatable to rotate the X-ray source about the z-axis to position the X-ray source at a plurality of different "cone beam view angles". Generally the rows of detectors in the detector array are perpendicular to the z-axis and the columns are parallel to the z-axis.

To image the ROI, the couch is moved along the z-axis to translate the ROI through a field of view (FOV) of the scanner, which is located between the scanner's X-ray source and detector array. As the ROI moves through the FOV the X-ray source is rotated around the z-axis to illuminate the ROI with X-rays at a plurality of different view angles. At each view angle and different axial positions of the ROI, detectors in the array of detectors measure intensity of X-rays from the source that pass through the ROI. The intensity of X-rays measured by a given detector in the array of detectors is a function of an amount by which X-rays are attenuated by material in the slice along a path length from the X-ray source, through the ROI to the given detector. The measurement provides information on composition and density of tissue in the ROI along the path-length.

The attenuation measurements for the ROI provided by the detectors are processed using algorithms known in the art to provide a map of the absorption coefficient of material in the ROI as a function of position. The map is used to display and identify internal organs and features of the region.

Ideally, each detector in a CT scanner measures intensity of X-rays that reach the detector after passage along a substantially straight-line path from the X-ray source to the detector. Therefore, ideally, the detector measures intensity of only those X-rays that are neither absorbed by the material along the path from the X-ray source to the detector nor scattered by the material at angles that prevent the X-rays from being incident on the detector. However, X-rays that are scattered out of a path from the X-ray source to one X-ray detector in the detector array of the CT scanner may be scattered in directions towards other X-ray detectors in the scanner' detector array. If these scattered X-rays are incident on the other X-ray detectors, they can generate error in measurements provided by the other detectors and degrade quality of an image provided by the CT scanner.

To reduce "scattering errors" in a CT scanner, X-ray detectors in the scanner's detector array are generally shielded from scattered X-rays by an anti-scattering (AS) collimator. The collimator generally comprises thin planar AS lamellae formed from a suitable X-ray absorbing material. In multi-slice scanners having a relatively small number of detector rows, the AS lamellae are generally located between columns of detectors but not between rows of detectors. The AS lamellae have their respective planes parallel to the z-axis and are oriented so that they intersect the focal spot of the X-ray source. In multislice scanners having a relatively large number of rows of detectors and a cone beam having a relatively large extent parallel to the z axis it has been found advantageous for an AS collimator to comprise AS lamellae between columns of detectors and also between rows of detectors. The AS lamellae between both the rows and columns have their respective planes oriented so that they intersect the focal spot of the X-ray source. An AS collimator for which the lamellae are located only between columns of detectors are referred to as a "1D" AS collimator. An AS collimator having lamellae between columns and rows of detectors are referred to as a "2D" AS collimator. A space in a 2D AS collimator through which X-rays may pass unhindered by the collimator's AS lamellae, which is surrounded on all sides by AS lamella and doesn't contain a smaller space surrounded on all sides by AS lamellae, is referred to as an "anti-scattering (AS) well".

Unpublished PCT application PCT/IL02/00729 filed Sep. 4, 2002, the disclosure of which is incorporated herein by reference describes different configurations of 2D AS collimators useable for multislice CT scanners.

U.S. Pat. No. 6,363,136 describes 2D AS collimators for a CT scanner formed from a plurality of shielding elements each comprising a base plate and a plurality of lamellae mounted perpendicular to the base plate. A plurality of the shielding elements are abutted one to the other so that the lamellae of one plate butt against the base plate of a next shielding element. The butted base plates are held in position by support plates having grooves that receive the base plates.

U.S. Pat. No. 4,054,800 entitled "Methods of Collimator Fabrication" shows various methods of producing "a collimator for radiation receiving and imaging devices". All the methods employ tenon and mortise like joints to couple components of the collimator. FIG. 6 in the patent shows foils of radiation absorbing material corrugated with slightly trapezoidal like corrugations to facilitate tenon and mortise joining of the corrugated foils one to the other. The joined strips are held together by compression in a suitable frame.

U.S. Pat. No. 3,943,366 entitled "Collimator for Ray Diagnosing Device" describes forming a honeycomb structure having hexagonal AS wells, very much like a bee honeycomb. The structure is formed from strips corrugated with corrugations having trapezoidal edge-on profiles so that the edge-on profile of each corrugation appears as three sides of a hexagon. The strips are glued together to form the honeycomb collimator.

U.S. Pat. No. 4,450,706 entitled "Method and Apparatus For Forming Collimator Strips" describes and shows a method of forming strips suitable for fabricating a honeycomb collimator similar to that described in U.S. Pat. No. 3,943,366. The method comprises pressing a strip of suitable deformable radiation absorbing material between matching male and female dies.

SUMMARY OF THE INVENTION

An aspect of some embodiments of the present invention relates to providing a 2D AS X-ray collimator and method of making the same for a CT scanner in which lamellae in the collimator form rectangular AS wells.

In accordance with an embodiment of the invention a strip of suitable heavy metal such as Tungsten (W) or Molybdenum (Mo) is precision "corrugated" to generate a strip of the metal, which when seen edge on might for example exhibit a shape of a train of rectangular and/or square pulses. That is, the "edge-on" profiles of the corrugations are rectangular or square. A plurality of the corrugated strips are aligned so that the protruding, "convex", sides of the corrugations of one strip are opposite the depression, "concave", sides of corrugations in an adjacent strip and bonded together to form a honeycomb structure of rectangular and/or square AS wells.

In an embodiment of the invention corners of the corrugations are chamfered to facilitate mortise joining the corrugations and providing lands for a bonding agent used to bond the strips together.

In an embodiment of the invention, each strip is aligned with and bonded to a flat strip of an X-ray absorbing metal so that the flat strip covers the concave sides of the corrugations on one side of the corrugated strip. The bonded corrugated and flat strips form an "intermediate unit" that is planar on one side and corrugated on the other. The units are aligned with the planar side one unit facing the corrugated side on a next unit and bonded together to form the 2D AS collimator.

There is therefore provided in accordance with an embodiment of the present invention, An X-ray collimator for collimating X-rays from an X-ray source that illuminate an array of columns and rows of X-ray detectors, the collimator having a first side that faces the X-ray source and a second side opposite the first side that faces the detector array, the collimator comprising: a plurality of strips formed from an X-ray absorbing material, wherein each strip is corrugated so that it has rectangular and/or square corrugations; and means for maintaining the plurality of strips one next to the other with the corrugations of one strip aligned with corrugations of an adjacent strip to form an array of rows and columns of square/ and or rectangular wells corresponding to the X-ray detectors in the array.

Optionally, the corrugations are aligned so that convex side of corrugations on one strip are aligned opposite the concave sides of corrugations of an adjacent strip. Optionally, corners of corrugations in a given strip butt up against corners of corrugations in the adjacent strip. Additionally or alternatively, the corners of corrugations are chamfered. Additionally or alternatively, the means for maintaining the plurality of strips aligned comprises a bonding agent that bonds corners of corrugations that butt up against each other together.

In some embodiments of the present invention, the convex sides of corrugations of one strip are aligned opposite and contiguous with the convex sides of corrugations of an adjacent strip. Optionally, the means for maintaining the plurality of strips aligned comprises a bonding agent that bonds contiguous regions of corrugations together.

In some embodiments of the invention, the means for maintaining the plurality of strips together comprises a frame having two parallel sides that face each other and are formed with mirror image slots that receive ends of the corrugated strips.

In some embodiments of the present invention, the X-ray collimator comprises a flat strip formed from an X-ray absorbing material sandwiched between every two corrugated strips. Optionally, the means for maintaining the plurality of strips aligned comprises a bonding agent that bonds each flat strip to the corrugated strips between which it is sandwiched. Additionally or alternatively, the means for maintaining the plurality of strips together comprises a frame having two parallel sides that face each other and are formed with mirror image slots that receive ends of the corrugated and flat strip.

In some embodiments of the present invention, the X-ray collimator comprises two flat strips aligned and parallel to the other flat strips each of which is contiguous to a different one of an outermost corrugated strip in the collimator. Optionally, the outermost flat strips protrude beyond the corrugated strips on the second side of the collimator.

In some embodiments of the present invention, the flat strips protrude beyond the corrugated strips on the first side of the collimator.

In some embodiments of the present invention, each corrugation comprises three planar lamellae having four edges and wherein lines coincident with the edges of the lamellae intersect substantially at a same point on a first side of the collimator. Optionally, the intersection point substantially coincides with a focal spot of the X-ray source.

In some embodiments of the present invention, the X-ray detector array is comprised in a CT scanner

BRIEF DESCRIPTION OF FIGURES

Non-limiting examples of embodiments of the present invention are described below with reference to figures attached hereto, which are listed following this paragraph. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION OF EXEMPLARY EMBODIMENTS

Figure 1:
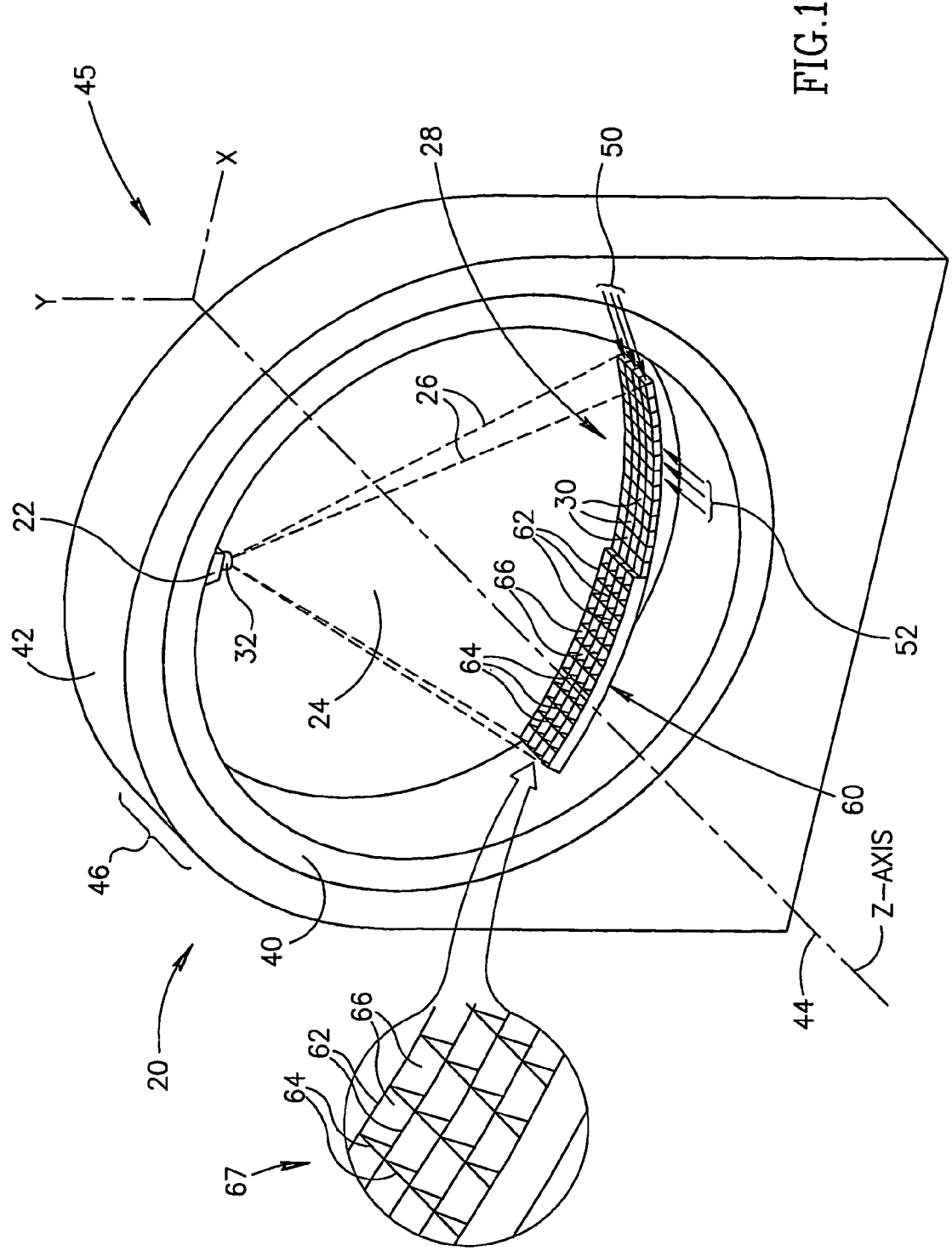
FIG. 1 schematically shows a CT scanner having a 2D AS collimator.

FIG. 1 schematically shows a multislice CT scanner 20 comprising an X-ray source 22 controllable to provide an X-ray cone beam 24, schematically indicated by dashed lines 26, and an array 28 of X-ray detectors 30. Cone beam 24 emanates from a focal spot 32 of X-ray source 22. X-ray source 22 and detector array 28 are mounted to a rotor 40, which in turn is rotatably mounted to a stator 42 so that the rotor can be rotated about an axis 44 conveniently labeled as the z-axis of a coordinate system 45. Stator 42 and rotor 40 are components of a gantry 46 of CT scanner 20. Only those features and components of CT scanner 20 germane to the present discussion are shown in FIG. 1.

Array 28 has rows 50 and columns 52 of X-ray detectors 30. The number of rows 50 and columns 52 of detectors 30 and the relative size of X-ray detectors 30 shown in detector array 28 is arbitrary and chosen for convenience and clarity of presentation. Detectors 30 in array 28 are shielded by a 2D AS collimator 60 which is shown partially cut away to show the detectors. AS collimator 60 comprises "row" lamellae 62 that are located between rows 50 of detectors 30 and "column" lamellae 64 that are located between columns 52 of detectors.

Lamellae 62 and 64 are optionally oriented so that their respective planes substantially intersect focal spot 32. Typically, lamellae 62 and 64 have thickness in a range from about 20 microns to about 100 microns and extend from array 28 towards focal spot 32 to a height in a range from about 20 millimeters to about 40 millimeters. Row and column lamellae 62 and 64 form AS wells 66. Optionally, a single X-ray detector lies at the "bottom" of a well 66. In some configurations, a plurality of X-ray detectors 30 lie at the bottom of a well 66. Row and column lamellae 62 and 64 and wells 66 of a portion of collimator 60 are shown enlarged for convenience of viewing in inset 67.

In practice, an X-ray detector array in a typical multi-slice CT scanner may comprise many thousands of small X-ray detectors 30 having areas typically equal to about a square millimeter configured in an array 28 comprising tens of detector rows 50 and many hundreds of detector columns 52. The X-ray detector array is generally formed from detector-modules each comprising a relatively small number of X-ray detectors 30 configured in a usually rectangular "mini-array" of rows 50 and columns 52 of detectors. Typically, the mini-array is a few centimeters long and a few centimeters wide and is mounted with to its own AS collimator. The modules are positioned one adjacent to and contiguous with the other to form the X-ray detector array.

Figure 2:
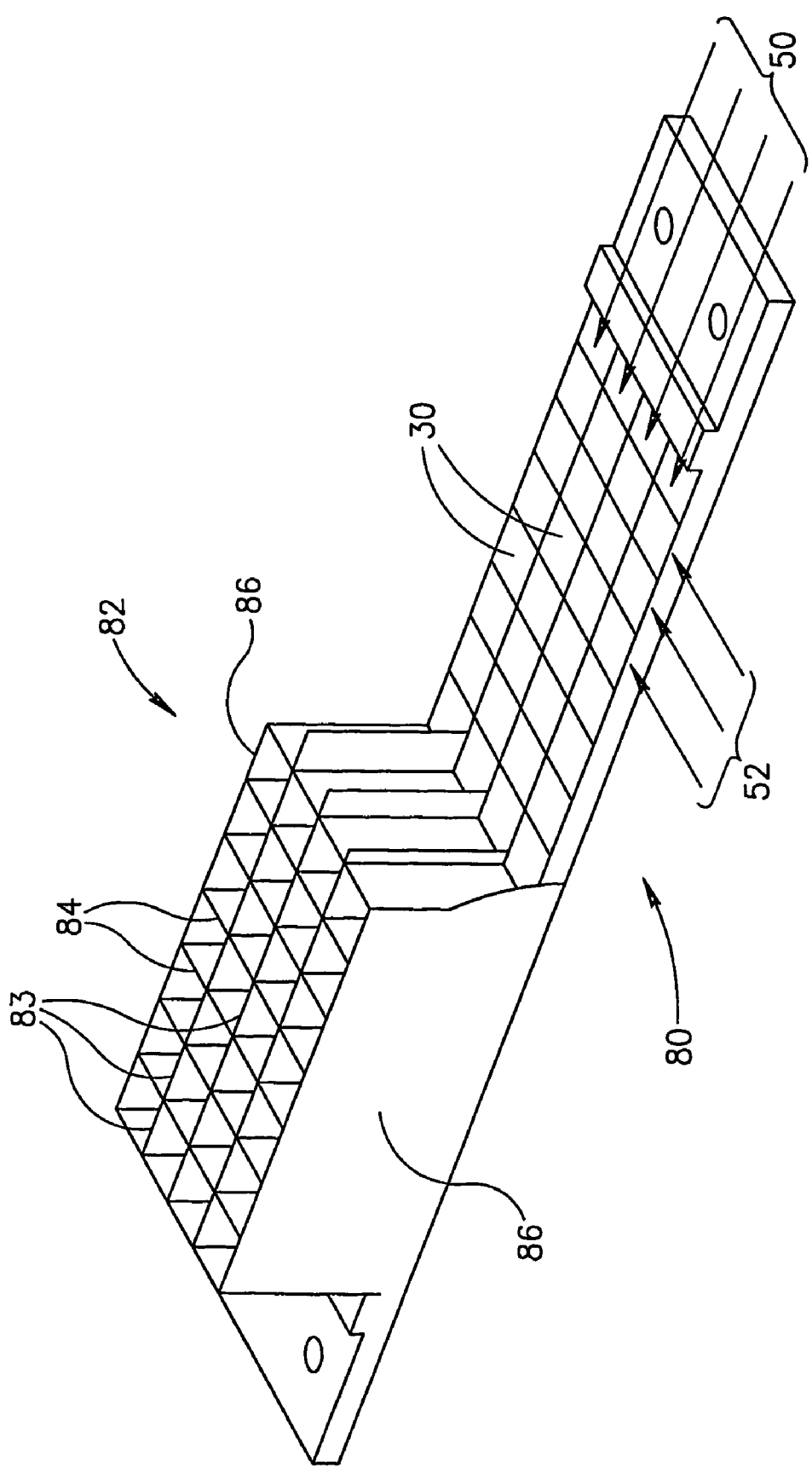
FIG. 2 schematically shows a detector module, which is a component of an X-ray detector array, comprising a plurality of X-ray detectors and its associated 2D AS collimator.

FIG. 2 schematically shows a detector module 80 and its associated 2D AS collimator 82, which is partially cut away to show detectors 30. AS collimator 82 comprises row lamellae 83 between rows 50 of detectors 30 and column lamellae 84 between columns 52 of the detectors. AS collimator 82 also comprises "outside" row lamella 86 that protrude on either side of detector module 80 below row and column lamellae 83 and 84. End lamellae 86 bracket detector module 80 between them and aid in aligning and mounting AS collimator 82 to the detector module.

FIGS. 3A-3E schematically show steps in a method of forming a 2D AS collimator for a detector module similar to detector module 80 shown in FIG. 2, in accordance with an embodiment of the present invention.

In a first step, each of a plurality of substantially rectangular strips of a material having a relatively high X-ray absorption coefficient, such as for example W or Mo, is precision "corrugated" so that it exhibits a plurality of corrugations. Each corrugation comprises three adjacent lamellae and viewed "edge on" appears as a square or rectangular upright or inverted "U". Each inverted U corrugation is adjacent an upright U corrugation and share a lamella. After corrugation, a cross-section through the corrugated strip parallel to its length resembles a train of rectangular or square pluses.

Figure 3A:
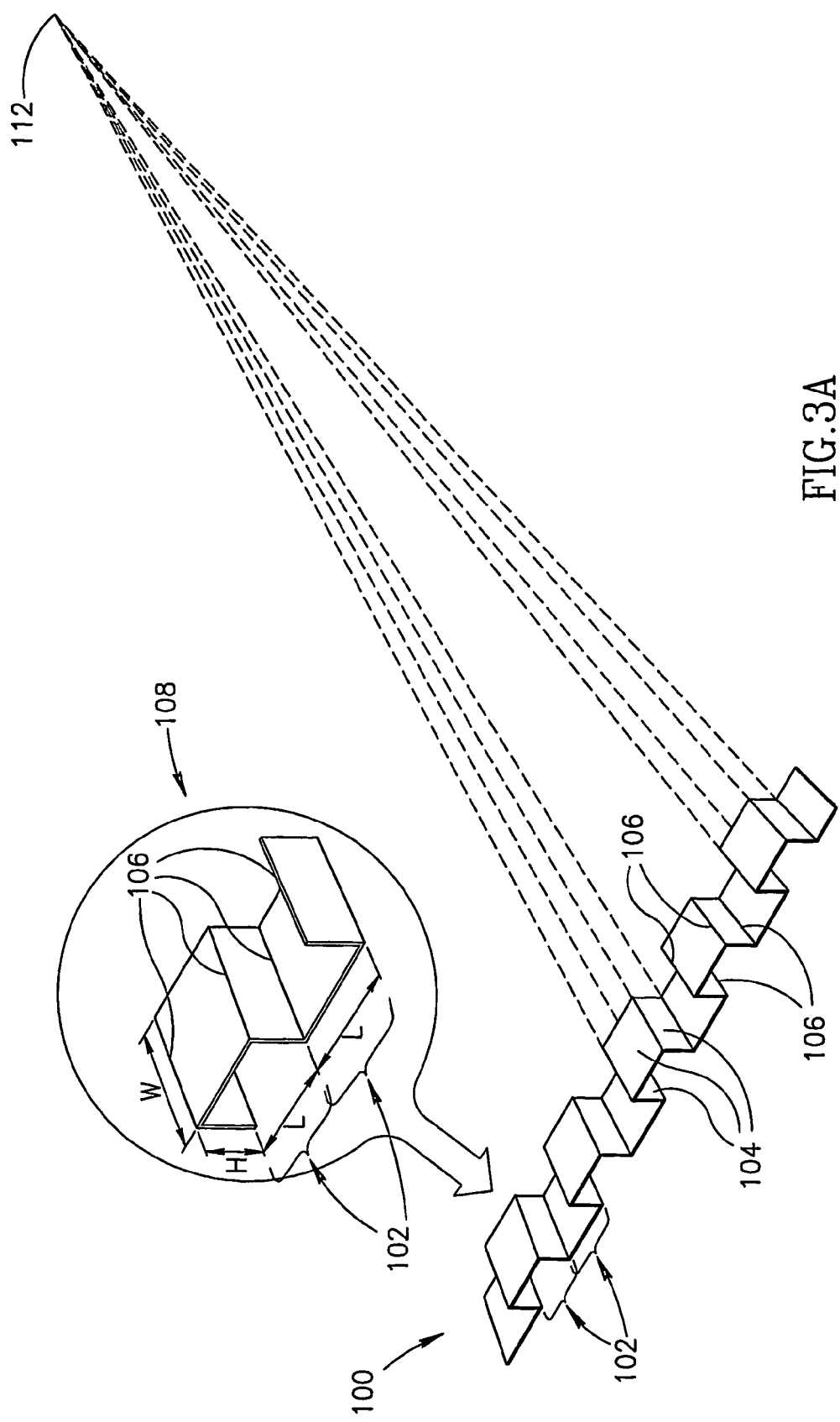
FIGS. 3A-3E schematically illustrate production of a 2D AS collimator in accordance with an embodiment of the present invention.

FIG. 3A schematically shows a strip 100 after it is corrugated so that it exhibits corrugations 102, in accordance with an embodiment of the invention. By way of example, in FIG. 3A each corrugation 102, seen edge-on, appears as a rectangular inverted or upright U, has three lamellae 104, edges 106 and has a length L and height H. Strip 100 has a width "W". Optionally, all corrugations 102 have a same length L.

Inset 108 schematically shows two adjacent corrugations 102 comprised in corrugated strip 100. A left most corrugation 102 in inset 108 seen edge on resembles an inverted U and a right most corrugation 102 seen edge on resembles an upright U. For convenience of presentation and to reduce clutter, only some lamellae 104 and edges 106 are labeled with their identifying numerals. Optionally, strip 100 is corrugated so that straight lines coincident with edges 106 of any corrugation 102 meet substantially at a same intersection point. The intersection point is located at a distance from a corrugation 102 that is substantially equal to a distance from an X-ray detector to a focal spot of a CT scanner in which an AS collimator formed from strip 100 is used. In FIG. 3A dashed lines 110 coincident with edges 106 of two corrugations 102 are drawn to indicate orientation of the edges and that they meet at a common intersection point 112. As a result of the orientation of edges 106 of a corrugation 102, the planes of lamella 104 of the corrugation pass substantially through the focal spot of the CT scanner in which the AS collimator formed from strip 100 is used. A side of a corrugated strip 100 facing intersection point 112 is referred to as an "X-ray source side" of the strip. A side of a corrugated strip facing away from intersection point 112 is referred to as a detector side of the strip.

Figure 3B:
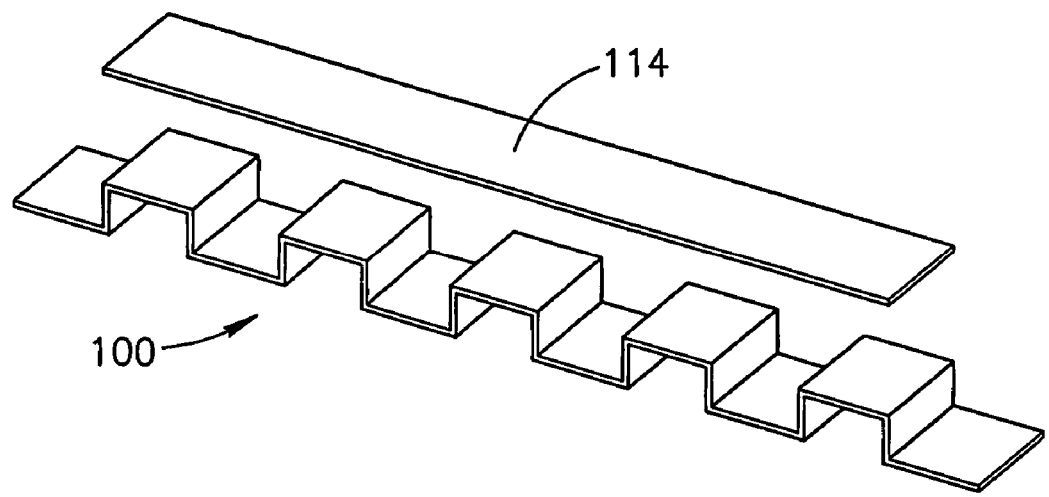
Figure 3C:
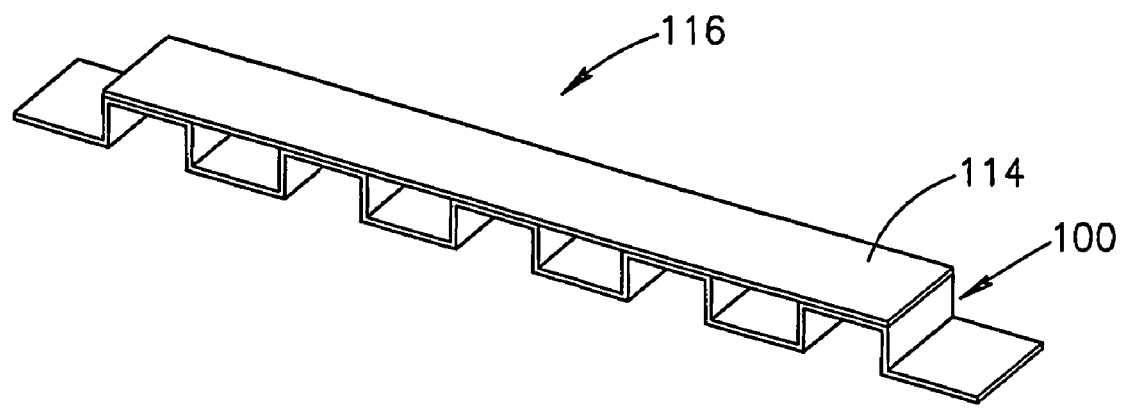

Optionally, each corrugated strip 100 is aligned with and bonded to a flat strip, hereinafter referred to as a "closure strip", formed from a material having a relatively high X-ray absorption coefficient, which is optionally the same material from which the corrugated strip is formed. FIG. 3B schematically shows a corrugated strip 100 and a flat closure strip 114 to which it is to be bonded. FIG. 3C schematically shows strip 100 bonded to closure strip 114 to form an "intermediate assembly" 116. A side of an intermediate assembly 116 on which a closure strip 114 is located is referred to as "closed side" of the assembly. A side opposite the closed side, which is not bonded to a closure strip 114, is referred to as an "open side" of the assembly. An appropriate boding agent, such as an epoxy that is not readily degraded by exposure to X-rays, is used to bond corrugated strip 100 to closure strip 114. Optionally, closure strip 114 and corrugated strip 100 have substantially a same width W. Optionally, closure strip 114 and corrugated strip 100 have a thickness in a range from about 20 microns to about 80 microns. Optionally closure strip 114 and corrugated strip 100 have a same thickness.

Figure 3D:
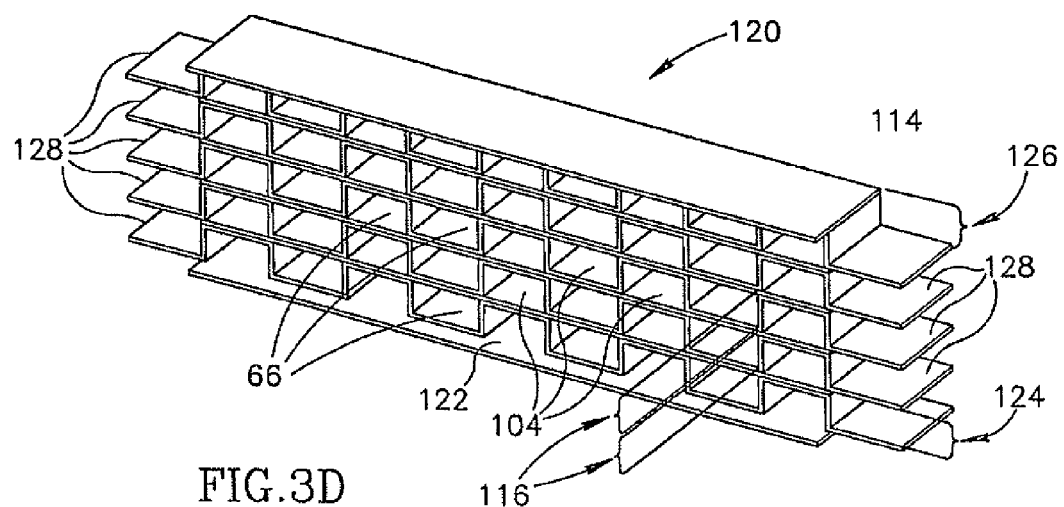

A plurality of intermediate assemblies 116 are aligned and bonded together with the closed side of one intermediate assembly facing the open side of an adjacent intermediate assembly and their respective X-ray source sides facing a same direction to form an AS collimator 120 shown in FIG. 3D. By way of example, intermediate assemblies 116 comprised in AS collimator 120 form rectangular wells 66. An additional closure strip 122 is bonded to the open side of a first intermediate assembly 124 in array 120 to "close off" open corrugations 102 in the intermediate assembly. Additional closure strip 122 and closure strip 114 (FIG. 3D) comprised in a last intermediate assembly 126 function as end row lamellae similar to end row lamellae 86 shown in FIG. 2. Closure strip 114 comprised in intermediate assembly 126 and additional closure strip 122 are optionally wider than the respective corrugated strips 100 to which they are bonded (FIG. 3C) and protrude slightly on the detector side of the corrugated strips.

Figure 3E:
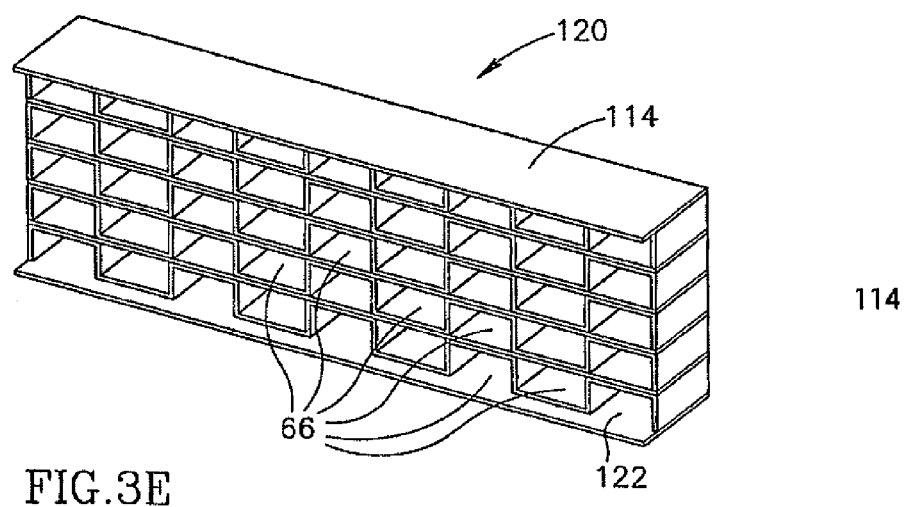

After trimming of protruding lamellae 128, collimator 120, as schematically shown in FIG. 3E, is suitable for mounting as a 2D AS collimator to an X-ray detector module, similar to module 80 shown in FIG. 2. Each rectangular well 66 in collimator 120 is suitable, for example, for providing X-ray collimation for a rectangular shaped X-ray detector or two square X-ray detectors having dimensions such that they fit at the bottom of the well.

It is noted that closure strips 114 and 122 used in producing AS collimator 120 provide ample lands for a bonding agent used to bond intermediate assemblies 116 together. In addition, depending upon an orientation of AS collimator 120 relative to rows and columns of detectors 30 in a detector module mounted with the AS collimator, closure strips 114 provide added shielding material between rows 50 or columns 52 of the X-ray detectors. In general, X-ray detectors in a detector array are exposed to a larger number of scattered X-rays from directions substantially transverse to the columns of the detector array than from directions substantially transverse to rows of the array. As a result it is usually advantageous to provide relatively more shielding material between columns of detectors than between rows of detectors.

In the above exemplary embodiment, closure strips 114 and 122 do not protrude beyond corrugated strips 100 on the X-ray source side of the collimator. However, in some collimators, as described in PCT Application PCT/IL02/00729 cited above, it can be advantageous to have lamellae between columns of detectors that extend on the X-ray source side of the collimator further than lamellae between rows of detectors.

Figure 4:
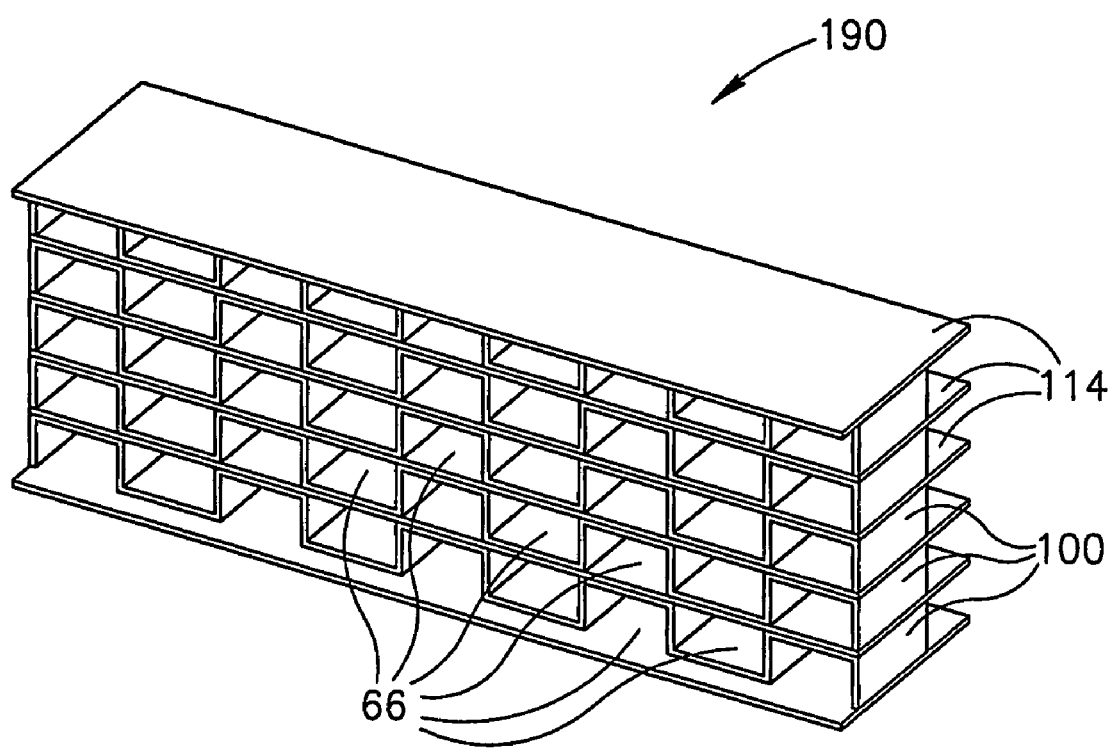
FIG. 4 schematically shows another configuration of a 2D AS collimator, in accordance with embodiments of the present invention.

FIG. 4 schematically shows a collimator 190 in which flat closure strips 114 extend on the X-ray source side of the collimator further than corrugated plates 100 in the collimator. As a result, collimator 190 has lamellae between columns of detectors in a corresponding detector array (not shown) that extend on the X-ray source side of the collimator further than lamellae between rows of detectors in the corresponding array. In the above description, AS collimator 120 is produced by first forming intermediate units 116 and then bonding the intermediate units together. In some embodiments of the present invention, corrugated strips 100, closure strips 114 and 122 are mounted to an appropriate jig and bonded together simultaneously to form AS collimator 120.

Figure 5A:
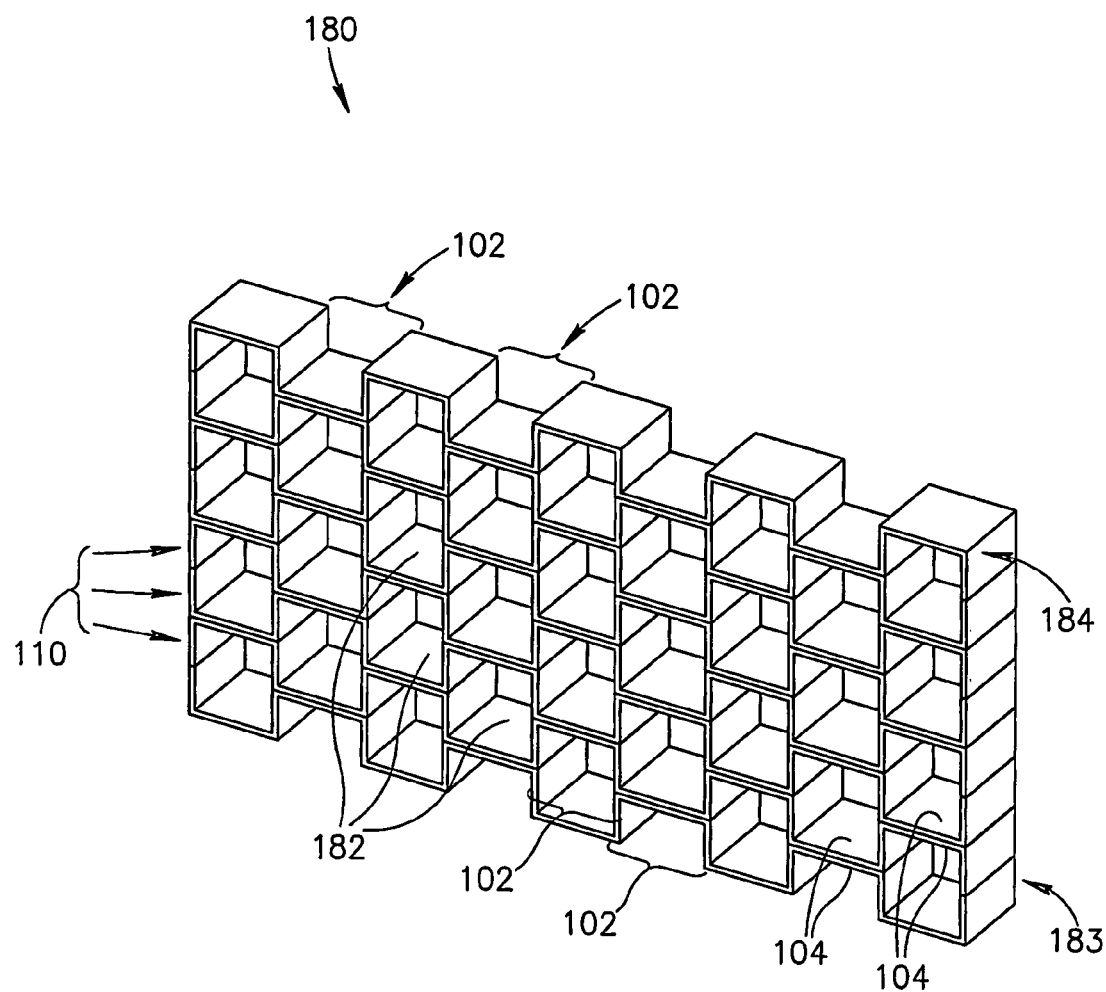
FIGS. 5A and 5B schematically show another configuration of a 2D AS collimator, in accordance with embodiments of the present invention.

FIG. 5A schematically shows another AS collimator 180 in accordance with an embodiment of the present invention. Collimator 180 is formed by aligning strips 100 one next to the other so that lamellae 104 (FIG. 3A) of protruding, convex, sides of corrugations 102 of one strip are opposite and contiguous with protruding lamellae 104 of convex sides of corrugations 102 in an adjacent strip. Contiguous lamellae 104 of adjacent strips 100 are bonded together using a suitable bonding agent and excess lamellae trimmed to form collimator 180 having wells 182.

Along a first outer corrugated strip 183 and a last outer corrugated strip 184 of collimator 180, corrugations 102 that are concave are open and do not form complete wells. In some embodiments of the invention the open corrugations are not used to form wells and collimator 180 is used to collimate X-rays in an array having detectors that correspond to wells 182.

Figure 5B:
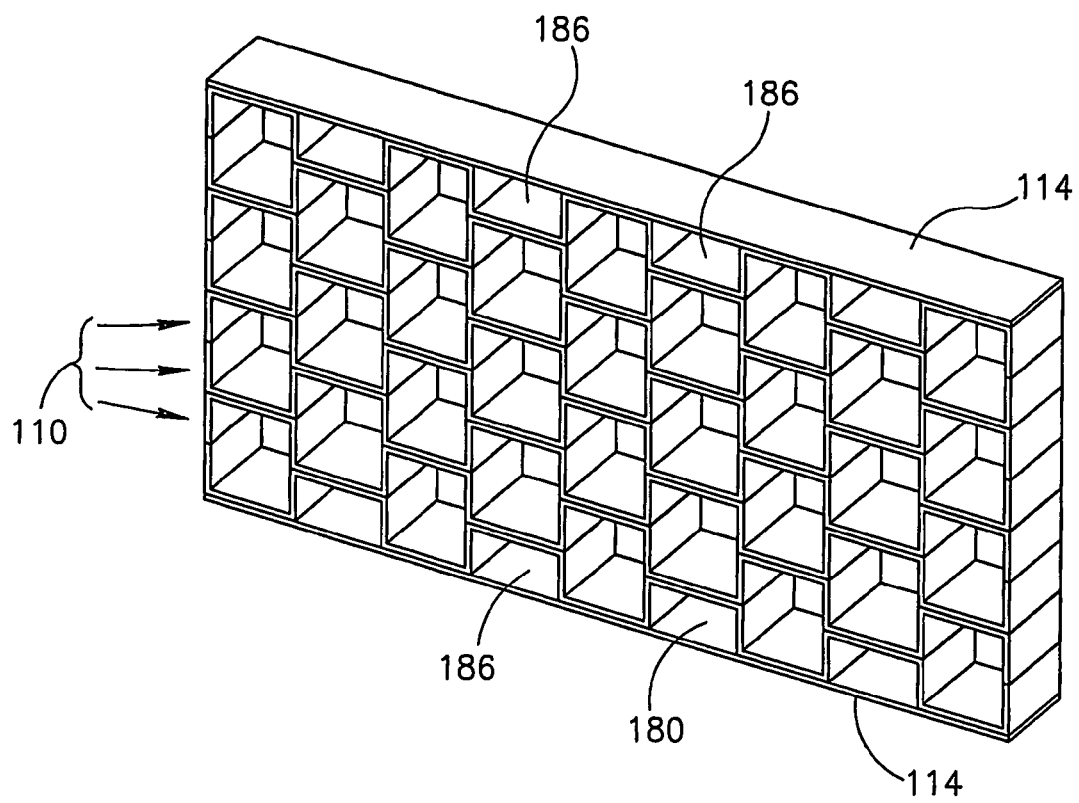

In some embodiments of the invention flat closure strips 114 are bonded to outer corrugated strips 183 and 184, as shown in FIG. 5B to close open concave corrugations 102 in the outer corrugated strips. When closed by closure strips 114 bonded to outer corrugated strips 183 and 184, the concave corrugations in the outer strips form "complete" wells 186 having cross sectional areas that are half that of wells 182.

In some embodiments of the invention, a plurality of collimators 180 are positioned side by side and contiguous with the other so that open concave corrugations 102 of adjacent collimators are directly opposite each other. Opposite open corrugations "close" each other and form complete wells that are substantially identical to wells 182. A plurality of collimators 180 placed side by side may thus be used to form a relatively long homogeneous collimator having substantially identical wells along its length.

Figure 6A:
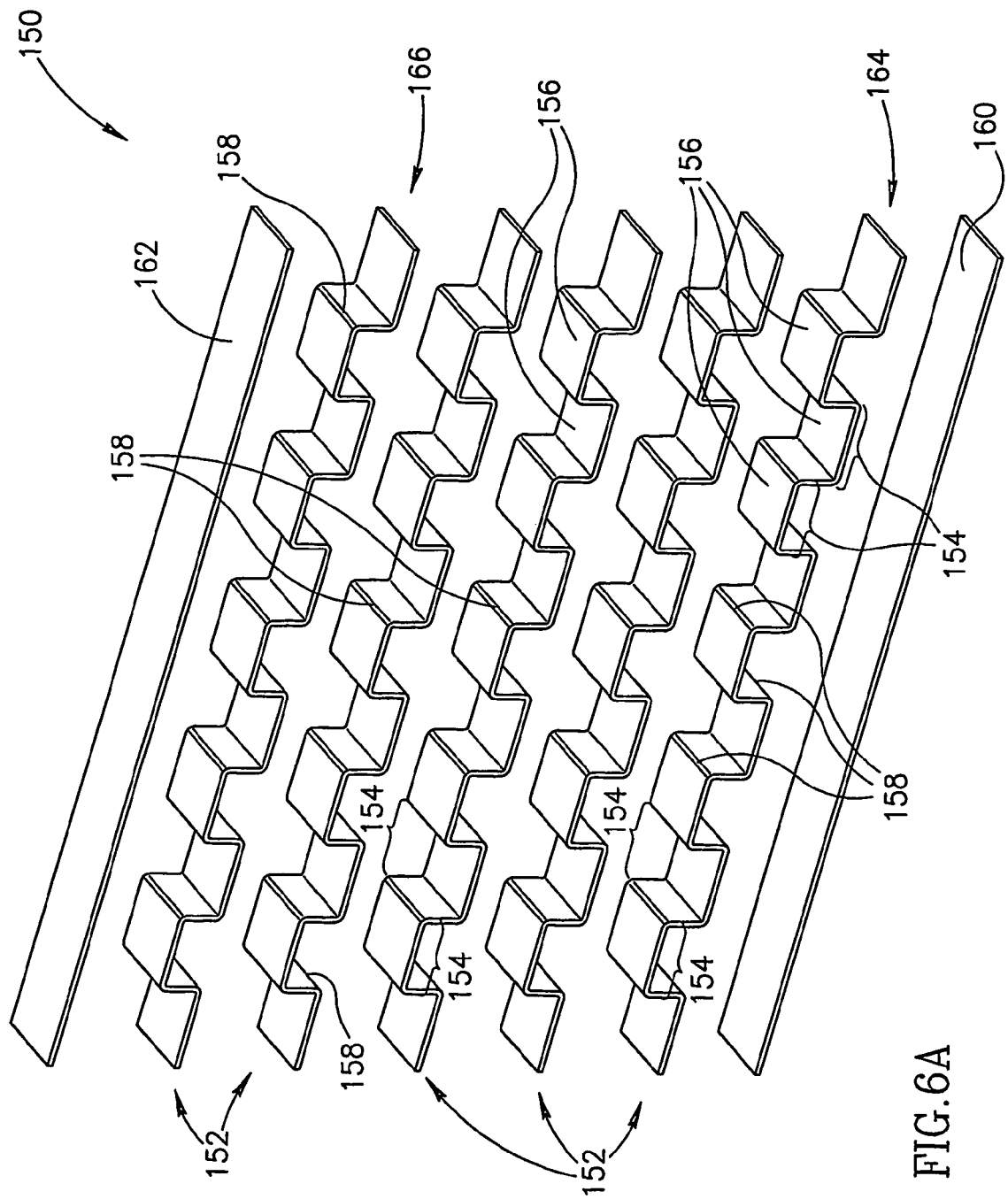
FIGS. 6A and 6B schematically show an exploded and assembled view of another AS collimator, in accordance with an embodiment of the present invention.
Figure 6B:
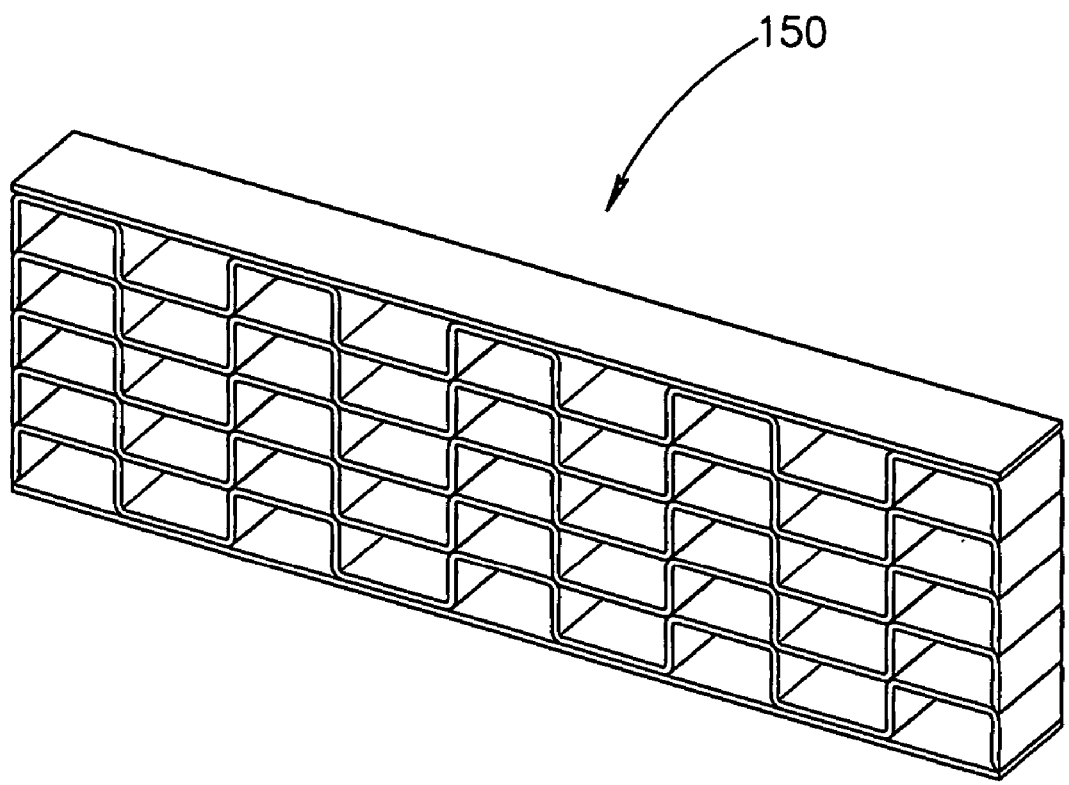

FIGS. 6A-6B schematically show an exploded view and an assembled view of another 2D AS collimator 150, in accordance with an embodiment of the present invention.

Collimator 150 is produced from a plurality of corrugated strips 152 having corrugations 154 comprising lamellae 156. Corrugated strips 152 are similar to corrugated strips 100 except that lamellae 156 have chamfered corners 158. In addition, corrugated strips 152 are not bonded to closure strips to provide lands for bonding the corrugated strips together and which remain between the corrugated strips in a collimator matrix. Instead, corrugated strips 152 are aligned so that the protruding, convex, sides of the corrugations of one strip are opposite the depressed, concave, sides of corrugations in an adjacent strip and chamfered corners 158 of the convex corrugations butt up against chamfered corners of the concave corrugations. The aligned corrugated strips 152 are bonded together using a suitable bonding agent applied to the chamfered corners, which provide lands for the bonding agent. Closure strips 160 and 162 are, optionally, bonded to a first and last corrugated strip 164 and 166 respectively in AS collimator 150 to "close" corrugations 154 in the strips.

After trimming excess material from matrix 150 the matrix, as shown in FIG. 6B is suitable for mounting to a matching X-ray detector module.

In some embodiments of the present invention corrugated strips, such as strips 100 (FIG. 3A) that are not formed with chamfered edges are aligned and bonded together similarly to the manner in which corrugated strips 152 are bonded together to form a collimator. When properly aligned with convex sides of the corrugations 102 of one strip 100 opposite concave sides of corrugations 102 in an adjacent strip 100 un-chamfered corners of the convex corrugations butt up against un-chamfered corners of the concave corrugations. While the un-chamfered corners provide smaller lands for a bonding agent than chamfered corners 158 of corrugated strips 152, the un-chamfered corners provide sufficient lands for a bonding agent used to bond the strips together.

Figure 7:
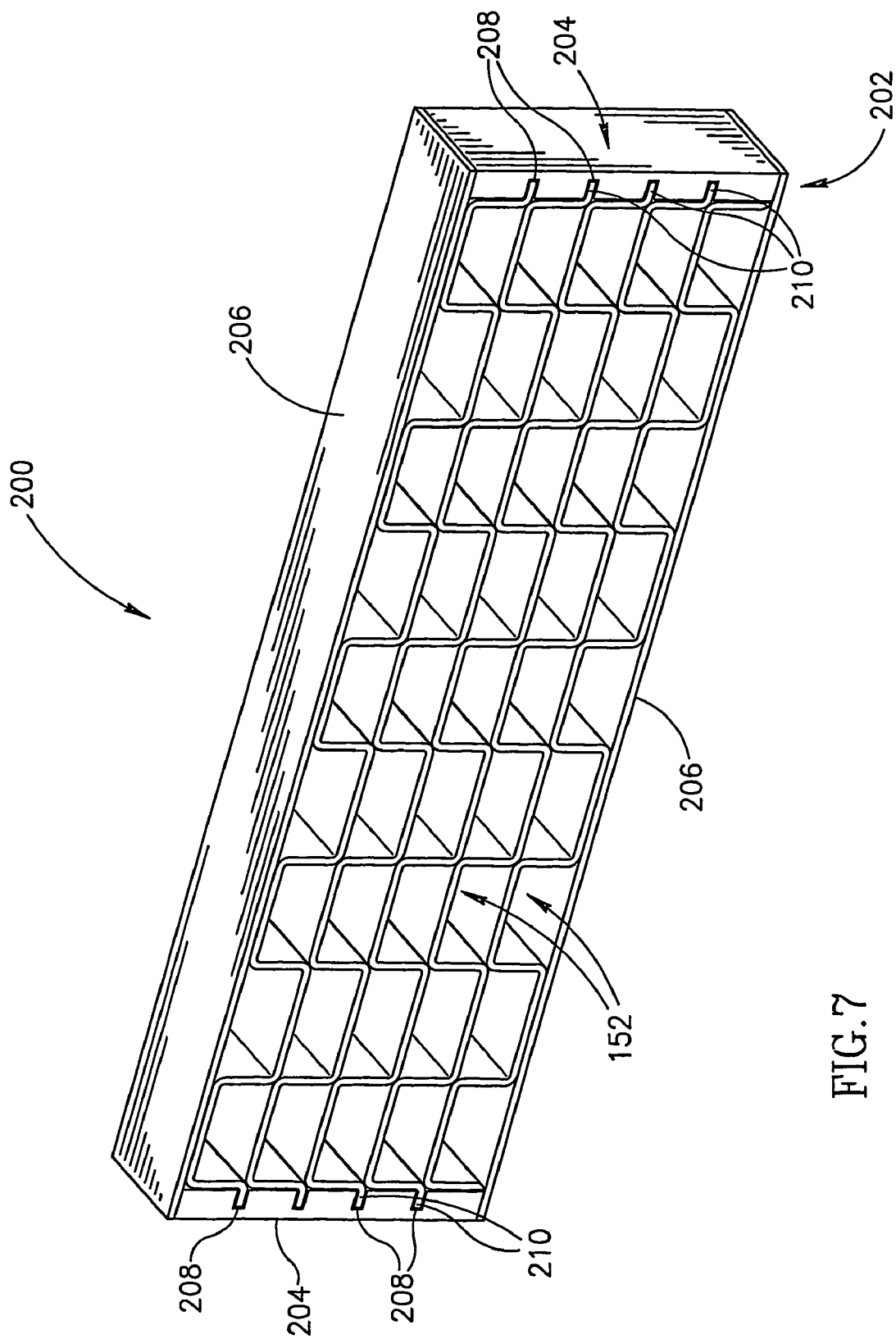
FIG. 7 schematically shows another AS collimator in accordance with an embodiment of the present invention.

In some embodiments of the present invention, corrugated strips, such as strips 100 shown in FIG. 3A or strips 152 shown in FIG. 6A are held in position by a suitable frame to from a collimator. FIG. 7 schematically shows, by way of example. a collimator 200 comprising strips 152 held together in a frame 202. Frame 202 comprises two registration bars 204 and optionally end lamellae 206, which registration bars and end lamellae are shown shaded in the figure. Registration bars 204 are formed with mirror image slots 208 that receive ends 210 of strips 152 and secure the strips properly positioned relative to each other.

A collimator in accordance with an embodiment of the invention comprising corrugated strips and flat strip between pairs of adjacent corrugated strips may also comprise a frame, which holds flat strips as well as corrugated strips in position. Slots in registration bars receive ends of both the corrugated and the flat strips.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. An X-ray collimator for collimating X-rays from an X-ray source that illuminate an array of columns and rows of X-ray detectors, the collimator having a first side that faces the X-ray source and a second side opposite the first side that faces the detector array, the collimator comprising:
   a plurality of strips formed from an X-ray absorbing material, wherein each strip is corrugated so that the strip has rectangular and/or square corrugations; and
   means for maintaining the plurality of strips one next to the other with the corrugations of one strip aligned with corrugations of an adjacent strip to form an array of rows and columns of square/and or rectangular wells corresponding to the X-ray detectors in the array.

2. An X-ray collimator according to claim 1 wherein the corrugations are aligned so that convex side of corrugations on one strip are aligned opposite the concave sides of corrugations of an adjacent strip.

3. An X-ray collimator according to claim 2 wherein corners of corrugations in a given strip butt up against corners of corrugations in the adjacent strip.

4. An X-ray collimator according to claim 2 wherein the corners of corrugations are chamfered.

5. An X-ray collimator according to claim 3 wherein the means for maintaining the plurality of strips aligned comprises a bonding agent that bonds corners of corrugations that butt up against each other together.

6. An X-ray collimator according to claim 1 wherein the convex sides of corrugations of one strip are aligned opposite and contiguous with the convex sides of corrugations of an adjacent strip.

7. An X-ray collimator according to claim 6 wherein the means for maintaining the plurality of strips aligned comprises a bonding agent that bonds contiguous regions of corrugations together.

8. An X-ray collimator according to claim 1 wherein the means for maintaining the plurality of strips together comprises a frame having two parallel sides that face each other and are formed with mirror image slots that receive ends of the corrugated strips.

9. An X-ray collimator according to claim 1 and comprising a flat strip formed from an X-ray absorbing material sandwiched between every two corrugated strips.

10. An X-ray collimator according to claim 9 wherein the means for maintaining the plurality of strips aligned comprises a bonding agent that bonds each flat strip to the corrugated strips between which the flat strip is sandwiched.

11. An X-ray collimator according to claim 9 wherein the means for maintaining the plurality of strips together comprises a frame having two parallel sides that face each other and are formed with minor image slots that receive ends of the corrugated and flat strip.

12. An X-ray collimator according to claim 1 and comprising two flat strips aligned and parallel to the other flat strips each of which is contiguous to a different one of an outermost corrugated strip in the collimator.

13. An X-ray collimator according to claim 12 wherein the outermost flat strips protrude beyond the corrugated strips on the second side of the collimator.

14. An X-ray collimator according to claim 9 wherein the flat strips protrude beyond the corrugated strips on the first side of the collimator.

15. An X-ray collimator according to claim 1 wherein each corrugation comprises three planar lamellae having four edges and wherein lines coincident with the edges of the lamellae intersect substantially at a same point on a first side of the collimator.

16. An X-ray collimator according to claim 15 wherein the intersection point substantially coincides with a focal spot of the X-ray source.

17. An X-ray collimator according to claim 1 wherein the X-ray detector array is comprised in a CT scanner.

18. The X-ray collimator according to claim 1 wherein the wells comprise square wells.

19. The X-ray collimator of claim 1, wherein corners of corrugations in a strip physically contact corners of corrugations in an adjacent strip.

20. A medical imaging system, comprising:
   an x-ray source that emits radiation that traverses an examination region;
   an x-ray detector the detects radiation that traverses the examination region; and
   an x-ray collimator located between the x-ray source and the x-ray detector, wherein the collimator collimates the emitted radiation, the collimator includes:
      at least two corrugated strips of x-ray absorbing material, wherein corners of corrugations of a first of the at least two strips directly contact and are bonded to corners of corrugations of a second of the at least two strips, and wherein each of the strips includes a rectangular shaped corrugation that forms a well that corresponds to the x-ray detector.

\* \* \* \* \*